United States Patent
McCague et al.

(10) Patent No.: US 10,913,962 B2
(45) Date of Patent: Feb. 9, 2021

(54) PROCESS OF MAKING (S)-NICOTINE

(71) Applicant: ZANOPRIMA LIFESCIENCES LIMITED, London (GB)

(72) Inventors: Raymond McCague, London (GB); Ashok Srinivasan Narasimhan, London (GB)

(73) Assignee: ZANOPRIMA LIFESCIENCES LIMITED, London (GB)

( * ) Notice: Subject to any disclaimer, the term of this patent is extended or adjusted under 35 U.S.C. 154(b) by 0 days.

(21) Appl. No.: 16/336,024

(22) PCT Filed: Mar. 12, 2019

(86) PCT No.: PCT/EP2019/056194
§ 371 (c)(1),
(2) Date: Mar. 22, 2019

(87) PCT Pub. No.: WO2020/098978
PCT Pub. Date: May 22, 2020

(65) Prior Publication Data
US 2020/0157589 A1  May 21, 2020

(30) Foreign Application Priority Data
Nov. 16, 2018 (EP) ..................................... 18206826

(51) Int. Cl.
*C12P 17/16* (2006.01)

(52) U.S. Cl.
CPC ........... *C12P 17/165* (2013.01); *C12Y 105/01* (2013.01)

(58) Field of Classification Search
CPC .... C07D 401/04; C12P 17/165; C12Y 105/01
See application file for complete search history.

(56) References Cited

U.S. PATENT DOCUMENTS

2016/0115150 A1* 4/2016 Arnold ................ C07D 401/04
546/279.4

FOREIGN PATENT DOCUMENTS

WO   WO 2014/174505 A2   10/2014
WO   WO 2016/065209 A2    4/2016

OTHER PUBLICATIONS

Weber et al. CAS: 171: 128332, 2019.*
Flora et al. Regulatory Toxicology and Pharmacology, 2016, 74:1-11.*
European Search Report issued in Application No. 18206826.2 dated Feb. 4, 2019.
Mitsukura et al., "A NADPH-dependent (S)-imine reductase (SIR) from *Streptomyces* sp. GF3546 for asymmetric synthesis of optically active amines: purification, characterization, gene cloning, and expression", Appl. Microbiol. Biotechnol., vol. 97, No. 18, Dec. 21, 2012, pp. 8079-8086.
Crooks, "Chemical properties of nicotine and other tobacco-related compounds", Analytical Determination of Nicotine and Related Compounds and their Metabolites, 1999, pp. 69-147 (79 pages).
Indian Office Action, dated Nov. 23, 2020, for Indian Application No. 202017029032, with an English translation.

* cited by examiner

*Primary Examiner* — Rei Tsang Shiao
(74) *Attorney, Agent, or Firm* — Birch, Stewart, Kolasch & Birch, LLP

(57) ABSTRACT

A process for synthetically producing (S)-nicotine ([(S)-3-(1-methylpyrrolidin-2-yl) pyridine]) is provided.

14 Claims, No Drawings

Specification includes a Sequence Listing.

PROCESS OF MAKING (S)-NICOTINE

FIELD OF THE INVENTION

The present invention relates to a process for synthetically producing (S)-nicotine ([(S)-3-(1-methylpyrrolidin-2-yl) pyridine]).

BACKGROUND OF THE INVENTION

Nicotine (3-[1-methylpyrrolidin-2-yl]pyridine) is a natural product that may be obtained from the leaves of Nicotiana, i.e. the tobacco plant. There is considerable demand for nicotine products across the tobacco industry and also across the pharmaceutical field. For example, there remains a demand for traditional tobacco products e.g. traditional cigarettes, which is likely due to the addictive nature of nicotine. However, due to growing concern around the detrimental impact of traditional cigarette products on consumer health, there is an increasing demand for tobacco replacement products containing nicotine, such as electronic cigarette devices, patches, lozenges, nasal spray and chewing gum. Tobacco replacement products may be provided as a substitute for traditional tobacco products that would otherwise result in harmful carcinogenic effects; such as due to the presence of pyridine alkaloids, polycyclic aromatics, phenols and N-nitrosamines. Tobacco replacement products may be used specifically to treat nicotine dependence. Within the pharmaceutical field, there is also interest in the possible therapeutic applications of nicotine.

Challenges exist for obtaining nicotine with suitable levels of both enantiomeric purity and chemical purity. Nicotine is optically active, i.e. it may exist in one of two possible enantiomeric forms: (R)-nicotine or (S)-nicotine. Processes for obtaining racemic mixes of nicotine exist (e.g. WO2016065209). However, it is acknowledged that (S)-nicotine (i.e. [(S)-3-(1-methylpyrrolidin-2-yl) pyridine]) is significantly more active than (R)-nicotine. Therefore, the demand in the tobacco industry and in the pharmaceutical field is for nicotine with a high level of enantiomeric purity with respect to the (S) enantiomer. The pharmaceutical industry in particular imposes strict regulations on the required level of enantiomeric purity for new pharmaceutical products, and it is possible that the existing required level of enantiomeric purity for nicotine may increase. In addition to the demand for enantiomeric purity of nicotine, obtaining a high level of chemical purity is also of importance in both the pharmaceutical and tobacco industries—chemical purity referring to the amount of nicotine (i.e. both (R) and (S) enantiomeric forms) in comparison to non-nicotine impurities. The pharmaceutical industry already imposes very strict regulations on the required level of chemical purity of nicotine in comparison to non-nicotine impurities. In fact, the current U.S. Pharmacopeia reference standard for the chemical purity of nicotine is at least 99% with not more than 0.5% of any single impurity. A high chemical purity is also of significant importance to the tobacco industry, as the harmful carcinogenic effects mentioned above can be caused by impurities that are capable of exerting a carcinogenic effect.

(S)-Nicotine may be obtained by extraction from leaves of the tobacco plant. However, when nicotine is obtained this way, it typically has a chemical purity of less than 95% due to the presence of related alkaloid impurities. A typical composition of a nicotine sample obtained by extraction from tobacco leaves comprises 93% (S)-nicotine, 2.4% (S)-nornicotine, 3.9% (S)-anatabine and 0.5% (S)-anabasine (E. Leete and M. Mueller, J. Am. Chem., Soc., 1982, 104, 6440-44). The alkaloid impurities are of a similar chemical structure to nicotine and consequently are difficult to remove. The actual composition of nicotine is also dependent on such factors as the geographic source and the season of harvest.

(S)-Nicotine may also be obtained by a synthetic process. There are various examples in the prior art for synthetically producing (S)-nicotine. For example, in the prior art are processes where a racemic (i.e. equal) mix of (R)-nicotine and (S)-nicotine is made, where this racemic mix is subsequently resolved to obtain the (S) enantiomer (U.S. Pat. No. 8,389,733, US 2014/0031554, and U.S. Pat. No. 8,378,111). There is also an example in the prior art of a synthetic process for producing (S)-nicotine using an enzyme as a biocatalyst (WO 2014/174505); the use of biocatalysts in enantiomerically selective processes in general are known outside of the nicotine field (L. S. Bleicher et al, *J. Org. Chem.*, 1998, 63, 1109-18, WO 2013/170050, WO2015/073555, P. N Scheller et al, *Chembiochem*, 2014, 15, 2201-4, Gand et al, *J Mol. Cat. B, Enzymatic*, 2014, 110, 126-32). Nevertheless, selectively synthesising (S)-nicotine in preference to the (R) enantiomer with high enantiomeric selectivity whilst also achieving high chemical purity remains a challenge.

SUMMARY OF THE INVENTION

In a first aspect, there is a process of making (S)-nicotine comprising the steps of:
(i) reducing myosmine with an enzyme with imine reductase activity to form (S)-nornicotine; and
(ii) methylating the (S)-nornicotine formed from step (i) to form (S)-nicotine.

It was surprisingly found that by way of steps (i) and (ii) of this process, where myosmine is used as the starting material, a very high enantiomeric and chemical purity was achieved for (S)-nicotine. This indicates that step (i) is a highly enantiomeric selective synthetic step with preference for the (S) isomer, and that step (ii) is such that this preference is retained in the final nicotine product, whilst also maintaining high chemical purity. This allows the production of (S)-nicotine without having to resort to resolution of a racemic mix. The high chemical purity is particularly advantageous; a reduced level of the undesirable impurities typically associated with nicotine results in a reduced risk of potential impurity-related negative effects. Furthermore, steps (i) and (ii) offer a convenient manufacturing process for making (S)-nicotine.

In a second aspect there is a process for producing a pharmaceutical composition, comprising forming (S)-nicotine using the process of the first aspect, and including the (S)-nicotine in the pharmaceutical composition together with one or more pharmaceutical excipients.

In a third aspect there is a process for producing a formulation for an electronic cigarette device, comprising forming (S)-nicotine using the process of the first aspect, and including the (S)-nicotine in a solvent with one or more additives.

In a fourth aspect there is the use of myosmine and an enzyme with imine reductase activity in a process of forming (S)-nicotine.

In a fifth aspect there is a kit comprising myosmine and an enzyme with imine reductase activity, for use in the above process of forming (S)-nicotine.

DESCRIPTION OF THE PREFERRED EMBODIMENTS

As the skilled person will appreciate, myosmine, (S)-nornicotine and (S)-nicotine, have the following structures:

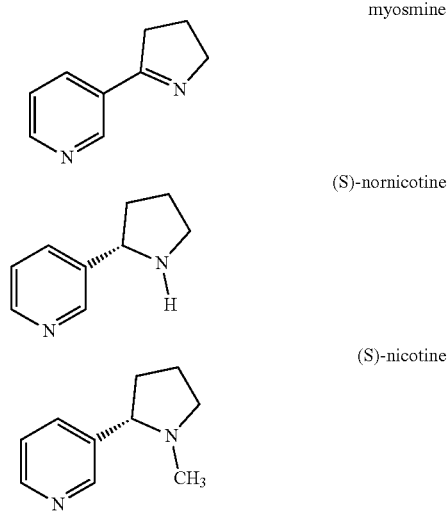

The skilled person will be familiar with appropriate reaction schemes to make myosmine.

As used herein, an "enzyme with imine reductase activity" refers to an enzyme capable of asymmetrically reducing an imine group, in particular a secondary imine group, to the corresponding amine group, in particular a secondary amine group. In particular, the enzyme with imine reductase activity used in the process disclosed herein is an enzyme capable of catalysing the conversion of myosmine to (S)-nornicotine. The skilled person is familiar with such enzymes. The enzyme may be added to the reaction mixture in a variety of forms, such as in the form of spray dried cells.

Preferably, the process uses an enzyme capable of converting myosmine to (S)-nornicotine such that the (S)-nornicotine is obtained with an enantiomeric excess of at least 90%, preferably at least 95%, more preferably at least 98%, most preferably at least 99%. Enantiomeric excess is measured in the manner given in the Examples. In the processes disclosed herein, this high enantiomeric excess is also achieved for the (S)-nicotine that is eventually achieved as the final product.

As the skilled person will appreciate, enzymes with imine reductase activity typically include NADH/NADPH dependent oxidoreductases, such as NADH/NADPH dependent dehydrogenases, and NADH/NADPH dependent imine reductases. NADH/NADPH dependent dehydrogenases include those referred to by enzyme classification number E.C.1.1.1, and include in particular 6-phosphogluconate dehydrogenases, referred to by enzyme classification number E.C.1.1.1.44. Imine reductases include those referred to with enzyme classification number E.C.1.5.1, in particular those referred to with enzyme classification number E.C 1.5.1.48.

Examples of different species of imine reductases include thiazolinyl imine reductase, dihydrofolate reductase, Δ¹—pyrroline-2-carboxylate reductase, Δ¹—piperideine-2-carboxylate reductase, sanguinarine reductase, and 1,2-dihydro reticuline reductase. Such enzymes can be isolated or derived from sources such as Streptomyces, Verrucosispora, Mesorhizobium, Yersinia, Pseudomonas, Candida albicans, Eschscholzia, and Papaver.

Examples of possible enzymes also include those disclosed in WO2013170050 (the contents of which are incorporated by reference).

The enzyme may be IRED_A, IRED_B, IRED_C, IRED_D, IRED_E, IRED_F, IRED_P, IRED_X, IRED_AB, IRED-20, or a homologue thereof. IRED_A, IRED_B, IRED_C, IRED_D, IRED_E, IRED_F, IRED_P, IRED_X, and IRED_AB are available from Enzymicals; IRED-20 is available from Almac Group. For example, in one embodiment, the enzyme is IRED_A, IRED_B, IRED_C, IRED_D, IRED_E, IRED-20, or a homologue thereof.

Disclosed herein, the enzyme may comprise an amino acid sequence according to any one of SEQ I.D. NO: 1, SEQ I.D. NO: 2, SEQ I.D. NO: 3, SEQ I.D. NO: 4, or a homologue thereof. In another embodiment, the enzyme comprises an amino acid sequence according to any one of SEQ I.D. NO: 1, SEQ I.D. NO: 2, SEQ I.D. NO: 3, or SEQ I.D. NO: 4.

As used herein, "a homologue thereof" means an enzyme comprising an amino acid sequence having at least 70%, 75%, 80%, 85%, 90%, 95%, 96%, 97%, 98% or 99% sequence identity to any one of the enzymes disclosed herein. For example, "a homologue thereof" can mean an enzyme comprising an amino acid sequence having at least 70%, 75%, 80%, 85%, 90%, 95%, 96%, 97%, 98% or 99% sequence identity to the amino acid sequence according to any one of SEQ I.D. NO: 1, SEQ I.D. NO: 2, SEQ I.D. NO: 3, or SEQ I.D. NO: 4.

As used herein, the term "sequence identity" refers to a relationship between two or more amino acid sequences. When a position in one sequence is occupied by the same amino acid residue in the corresponding position of the comparator sequence, the sequences are said to be "identical" at that position. The percentage "sequence identity" is calculated by determining the number of positions at which the identical amino acid residue occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window. In order to optimally align sequences for comparison, the portion of a polypeptide sequence in the comparison window may comprise additions or deletions termed gaps while the reference sequence is kept constant. An optimal alignment is that alignment which, even with gaps, produces the greatest possible number of "identical" positions between the reference and comparator sequences. Levels of sequence identity between coding sequences may be calculated using known methods.

The sequence identity can be calculated using publicly available computer-based methods for determining sequence identity including the BLASTP, BLASTN and FASTA (Atschul et al., J. Molec. Biol., 215: 403-410, (1990)), the BLASTX programme available from NCBI, and the Gap programme from Genetics Computer Group (Madison Wis.). Levels of sequence identity are obtained using the Gap programme, with a Gap penalty of 50 and a Gap length penalty of 3 for the amino acid sequence comparisons.

Generally, step (i) comprises reducing myosmine with the enzyme in the presence of a suitable cofactor, in particular NADH or NADPH. As the skilled person will appreciate, the enzyme and the cofactor may be introduced to the reaction mixture as separate components, or they may be introduced to the reaction mixture as part of the same component for example in the form of whole microbial cells which contain both the enzyme and the appropriate cofactor. A suitable cofactor recycling system may be present to convert the cofactor from its oxidised form (NAD+ or NADP+) to its reduced form (NADH or NADPH). The skilled person will be familiar with appropriate cofactor recycling systems, such cofactor recycling systems including glucose(monohydrate)/glucose dehydrogenase, formate/formate dehydrogenase and isopropanol/alcohol dehydrogenase. When a cofactor recycling system is present, the cofactor may be added to the reaction mixture in its oxidised form i.e. as NAD+ or NADP+.

The cofactor itself may be present in the range of 0.02 parts to 10 parts by weight per 100 parts of myosmine. Preferably, the cofactor may be present in the range of 0.05 part to 5 parts by weight per 100 parts of myosmine. More preferably, the cofactor may be present in the range of 0.5 part to 2 parts by weight per 100 parts of myosmine.

The amount of enzyme present in step (i) can be present in an amount of 0.1 parts to 30 parts by weight per 100 parts of myosmine. Preferably, the amount of enzyme present in step (i) can be present in an amount of 0.5 parts to 10 parts by weight of myosmine. The skilled person will appreciate that the amount of enzyme present in step (i) can be tailored depending on the desired time period for the reaction of step (i), where more enzyme can be used for a shorter reaction time, and vice versa.

Step (i) may be carried out in the presence of an ion exchange resin, however preferably step (i) is carried out in absence of an ion exchange resin. The ion exchange resin, when present, is an Amberlite resin, an Amberlyst resin, an Amberjet resin, such as Amberlite IR-120, or a Dowex resin, where each of these ion exchange resins is available from Aldrich.

The possible pH for step (i) can be in the range of pH 5-9.

The (S)-nornicotine is converted to (S)-nicotine by a further step of: (ii) methylating the (S)-nornicotine formed from step (i) to form (S)-nicotine.

It was surprisingly found that following step (ii) the (S)-nicotine was achieved with particularly high chemical purity and particularly high enantiomeric excess.

The methylation step, i.e., step (ii), may be carried out by way of a muti-step process. For example, step (ii) may comprise forming a compound (e.g. N-formyl-(S)-nornicotine), and then subsequently reducing this compound to arrive at the methylated product i.e. (S)-nicotine. Preferably however, step (ii) is carried out by way of a single step process such as reductive methylation. As the skilled person will appreciate, the term "reductive methylation" refers to a process whereby a species is formed and reduced to arrive at the methylated product (i.e. (S)-nicotine) by way of a single step.

Preferably, the (S)-nornicotine is reductively methylated using formaldehyde or a formaldehyde-based compound. Step (ii) is particularly effective when using such reagents.

As used herein, a formaldehyde-based compound is used to refer to a compound that is capable of generating formaldehyde in-situ during a chemical reaction. The skilled person will appreciate that this means the formaldehyde-based compound is added to the reaction mixture, and then subsequently breaks down to release formaldehyde (and other related compounds) which may then react with the (S)-nornicotine to form (S)-nicotine. In the case of the addition of a formaldehyde-based compound, the skilled person will be familiar with how to tailor the appropriate amount of the formaldehyde-based compound added in order to achieve the release of a particular amount of formaldehyde in situ.

Formaldehyde itself has the formula HC(O)H and is generally introduced as a liquid or a gas. The formaldehyde may be introduced to the reaction mixture as part of an aqueous solution of formaldehyde (such aqueous solutions may be referred to as formalin).

The formaldehyde-based compound is generally introduced as a solid or a liquid. The formaldehyde-based compound may be a dimer of formaldehyde, a polymer of formaldehyde, or an acetal of formaldehyde. Preferably, the formaldehyde-based compound is a polymer of formaldehyde.

As the skilled person will appreciate, the term "polymer of formaldehyde" refers to a compound with three or more polymerised formaldehyde repeat units. Preferably, the polymer of formaldehyde is paraformaldehyde. As used herein, the term "paraformaldehyde" refers to polymer of formaldehyde with a degree of polymerization of 8-100 units.

When the (S)-nornicotine is reductively methylated using formaldehyde or a formaldehyde-based compound, the formaldehyde or formaldehyde-based compound may be added in an amount of 50 parts to 110 parts by weight, preferably 60 parts to 90 parts by weight, per 100 parts of (S)-nornicotine. Such amounts refer to the actual amounts of formaldehyde, formaldehyde-based compound and (S)-nornicotine present. Therefore, where for example the (S)-nornicotine is formed as part of a solution (e.g. an aqueous solution) and/or when the formaldehyde or formaldehyde-based compound is introduced to the reaction mixture as part of a solution (e.g. an aqueous solution) the parts by weight disclosed herein refer to the actual amounts of the formaldehyde, formaldehyde-based compound and (S)-nornicotine contained in the respective solutions.

Where the methylation step is a reductive methylation step, the reductant may be formic acid, sodium cyanoborohydride, or palladium/hydrogen, preferably formic acid. As the skilled person will appreciate, the appropriate amount of reductant will depend on the specific reductant used. For example, when the reductant is formic acid, the reductant may be present in an amount of 40-110 parts, preferably 40-100 parts, more preferably 50 parts to 70 parts by weight per 100 parts of (S)-nornicotine. Such amounts refer to the actual amounts of reductant and (S)-nornicotine present.

Preferably, steps (i) and (ii) may be carried out without isolating the (S)-nornicotine formed from step (i). This allows the formation of (S)-nicotine with both a high enantiomeric excess and a high chemical purity whilst using a particularly convenient synthetic route. Avoiding the need for isolation of the (S)-nornicotine from the reaction mixture formed from step (i) before converting this to (S)-nicotine has the benefit of offering a particularly convenient synthetic route, as isolation of the (S)-nornicotine can be process intensive as a result of costly plant time and energy (for example due to the need for large quantities of solvent for extraction and/or the boiling down of the solution). For example, in step (i) the (S)-nornicotine may be formed as part of an aqueous solution, where the aqueous solution containing the (S)-nornicotine is then carried through for direct use in step (ii). Consequently, the methylation step (step (ii)) is performed on the aqueous solution of (S)-nornicotine formed from step (i). When the process is carried out in this manner, it is preferable for the (S)-nornicotine to be reductively methylated either by using paraformaldehyde, or, by using formaldehyde that is introduced to the reaction mixture as part of an aqueous solution. When the process is carried out in this manner, it is more preferable for the (S)-nornicotine to be reductively methylated by using formaldehyde that is introduced to the reaction mixture as part of an aqueous solution, as it has been found that this reduces undesirable frothing of the reaction mixture as the process proceeds.

The (S)-nicotine produced using the processes disclosed herein has an enantiomeric excess of at least 90%, preferably of at least 95%, more preferably of at least 98%, most preferably of at least 99%. The skilled person will be familiar with how to measure the enantiomeric excess. Enantiomeric excess may for instance be measured in the manner given in the Examples.

The (S)-nicotine produced using the processes disclosed herein has a chemical purity of at least 98%, preferably of at least 99%. The skilled person will be familiar with how to measure the chemical purity. Chemical purity may for instance be measured in the manner given in the Examples. The level of chemical purity achieved by the examples is particularly high.

The (S)-nicotine produced using the method steps above may be included in a pharmaceutical composition together with one or more pharmaceutical excipients. Preferably, the pharmaceutical composition is a transdermal patch, a lozenge, or an inhalation formulation.

The (S)-nicotine produced using the method steps above may also be included in a formulation for inclusion in an electronic cigarette device. The formulation includes (S)-nicotine in a solvent with one or more additives. The solvent may comprise glycerol, propylene glycol, water, or mixtures thereof.

Preferably, the solvent comprises glycerol and propylene glycol, wherein the proportion of glycerol to propylene glycol is in the range of 80:20 to 20:80 by volume. The one or more additives may include one or more flavouring agents.

Also provided herein is a kit comprising myosmine and an enzyme with imine reductase activity for use a process of forming (S)-nicotine.

A particularly preferred reaction scheme is displayed below as scheme 1:

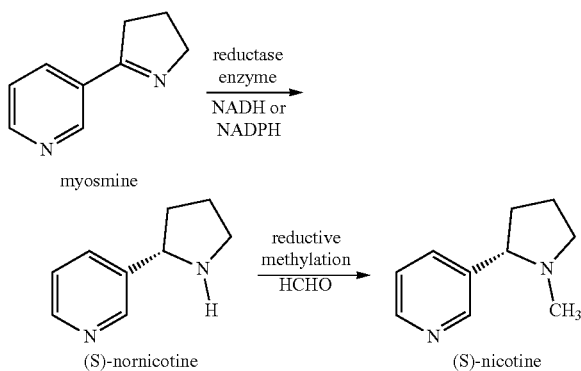

The invention will be demonstrated with the following non-limiting examples.

EXAMPLES

The following examples demonstrate results associated with the process disclosed herein. Various reagents have been used to exemplify the process.

The enzymes used include the following:

IRED_A from Verrucosispora maris (strain AB-18-032, Uniprot:

F4F8G5_VERMA) with the amino acid sequence (a) or (b) given below—sequence (a) corresponds with SEQ I.D. NO: 1, and sequence (b) corresponds with SEQ I.D. NO: 2.

(a) As used with hexahistidine tag, total 302 amino acid residues:

MHHHHHHAADSRAPVTVIGLGAMGSALARAFLAAGHPTTVWNRSPDKA

DDLVGQGAVRAATVADAMSAGNLIVICVLDYRAMREIIDSTGHSPADR

VIVNLTSGTPGDARATAAWAQEQGMEYIDGAIMATPSMIGSEETLIFY

GGPQEVYDAHADTLRSIAGAGTYLGEEPGLPSLYDVALLGLMWTTWAG

FMHSAALLASEKVPAAAFLPYAQAWFEYVISPEVPNLATQVDTGAYPD

NDSTLGMQTVAIEHLVEASRTQGVDPTLPEFLHARAEQAIRRGHAGDG

FGAVFEVLRAPAAQ (b) Original enzyme, total of 296 amino acid residues:

MAADSRAPVTVIGLGAMGSALARAFLAAGHPTTVWNRSPDKADDLVGQ

GAVRAATVADAMSAGNLIVICVLDYRAMREIIDSTGHSPADRVIVNLT

SGTPGDARATAAWAQEQGMEYIDGAIMATPSMIGSEETLIFYGGPQEV

YDAHADTLRSIAGAGTYLGEEPGLPSLYDVALLGLMWTTWAGFMHSAA

LLASEKVPAAAFLPYAQAWFEYVISPEVPNLATQVDTGAYPDNDSTLG

MQTVAIEHLVEASRTQGVDPTLPEFLHARAEQAIRRGHAGDGFGAVFE

VLRAPAAQ

IRED_B from Mesorhizobium sp. L48C026A00 aka a 6-phosphogluconate dehydrogenase, with the amino acid sequence (a) or (b) given below—sequence (a) corresponds with SEQ I.D. NO: 3, and sequence (b) corresponds with SEQ I.D. NO: 4.

(a) As used with hexahistidine tag, total 310 amino acid residues:

MHHHHHHASNVCVLGAGRMGSSIARTLLDRGYPTWVWNRTAAKCEPLA

ALGAKVASSVQEGIQAAEVVIINVLDYAASDALLKRDGIASALAGKAV

VQLTSGSPRLAREEARWVEAHGAGYLDGAIMATPDFIGKPETAMLYSG

SRDVYEKHKPLLFALGGGTNYVGELPGQASALDTALLTQMWGGLFGAL

QGMAVAEAEGLDLETFRNHLSAFKPVVDASLFDLVDRTNARRFAGDDA

TLASLGAHYSAFQHLLEACEERGLDAAMPRAMDMIFRQALSLGSMEDD

LASLALLFRNGSPRQSREPANA (b) Original enzyme, total of 304 amino acid residues

MASNVCVLGAGRMGSSIARTLLDRGYPTWVWNRTAAKCEPLAALGAKV

ASSVQEGIQAAEVVIINVLDYAASDALLKRDGIASALAGKAVVQLTSG

SPRLAREEARWVEAHGAGYLDGAIMATPDFIGKPETAMLYSGSRDVYE

-continued

KHKPLLFALGGGTNYVGELPGQASALDTALLTQMWGGLFGALQGMAVA

EAEGLDLETFRNHLSAFKPVVDASLFDLVDRTNARRFAGDDATLASLG

AHYSAFQHLLEACEERGLDAAMPRAMDMIFRQALSLGSMEDDLASLAL

LFRNGSPRQSREPANA

Example 1

Biotransformations were undertaken at 0.5 mL scale with a solution of 10 mM myosmine and NADP+(0.5 mM), glucose (25 mM), glucose dehydrogenase (10 U/ml), and the enzyme with imine reductase activity. The enzymes used are detailed in table 1, available from Enzymicals. For each enzyme, the amount of enzyme was 9 mg/ml of cell free extract (estimated approx. 0.9 mg/ml contained enzyme). For IRED_B and IRED_C specifically, additional tests were run which used 0.9 mg/ml cell free extract.

The enantiomeric excess of the (S) nornicotine obtained from the biotransformation was determined using a Chiralpak AD-H column (250×4.6 mm id) eluting with a mixture of hexane:ethanol:diethylamine 74.9:25.0:0.1 (v/v/v) at 1 ml/min over 18 min at 30° C. This method was also used to measure the conversion of myosmine into nornicotine, a relative response factor of 2.18:1 having been determined for uv absorption detection at 254 nm.

The results are displayed in table 1 below.

TABLE 1

| | Enzyme | Amount | Conversion [%] | Enantiomeric Excess [% S] |
|---|---|---|---|---|
| i | IRED_A | 9 mg/ml | 99.3 | 99.8 |
| ii | IRED_B | 9 mg/ml | 99.9 | 98.4 |
| iii | IRED_B | 0.9 mg/ml | 99.3 | 98.4 |
| iv | IRED_C | 9 mg/ml | 99.3 | 92.9 |
| v | IRED_C | 0.9 mg/ml | 100.0 | 99.1 |
| vi | IRED_D | 9 mg/ml | 99.6 | 99.8 |
| vii | IRED_E | 9 mg/ml | 99.4 | 99.8 |
| viii | IRED_F | 9 mg/ml | 99.1 | 86.5 |
| ix | IRED_P | 9 mg/ml | 97.7 | 86.6 |
| x | IRED_X | 9 mg/ml | 99.8 | 95.7 |
| xi | IRED_AB | 9 mg/ml | 99.6 | 96.8 |

The % enantiomeric excess for (S)-nornicotine was identified according to the equation [(S)−(R)]/((S)+(R)]×100 where (S) and (R) are the amounts of (S) and (R) enantiomers present respectively. The % conversion was identified according to the amount of myosmine consumed i.e. according to the equation 100−(final amount of myosmine)/(starting amount of myosmine)×100.

Example 2

Reactions were carried out in a similar manner to that of example 1, except that 1.5 equivs glucose and 1 mol % NADP+ were used relative to the myosmine substrate, and a 24 hr reaction time was employed. The enzymes used are detailed in each of tables 2, 3 and 4 (available from Enzymicals).

At 100 mM myosmine concentration, using 0.9 mg/mL enzyme cell free extract, the results were as displayed in the table below:

TABLE 2

| | Enzyme | Conversion [A] | Enantiomeric Excess [% S] |
|---|---|---|---|
| i | IRED_A | 63.6 | 99.8 |
| ii | IRED_B | 99.9 | 98.7 |
| iii | IRED_C | 99.9 | 99.8 |
| iv | IRED_D | 99.0 | 99.9 |
| v | IRED_E | 99.9 | 99.9 |

At 100 mM myosmine concentration, using 9 mg/mL enzyme cell free extract, the results were as displayed in the table below:

TABLE 3

| | Enzyme | Conversion [A] | Enantiomeric Excess [% S] |
|---|---|---|---|
| i | IRED_A | 99.9 | 99.8 |
| ii | IRED_B | 99.8 | 98.8 |
| iii | IRED_C | 99.8 | 99.9 |
| iv | IRED_D | 99.9 | 100.0 |
| v | IRED_E | 99.9 | 99.9 |

At 250 mM myosmine concentration, using 9 mg/mL enzyme cell free extract, the results were as displayed in the table below:

TABLE 4

| | Enzyme | Conversion [A] | Enantiomeric Excess [% S] |
|---|---|---|---|
| i | IRED_A | 100.0 | 99.7 |
| ii | IRED_B | 99.9 | 98.6 |
| iii | IRED_C | 100.0 | 99.9 |
| iv | IRED_D | 100.0 | 99.9 |
| v | IRED_E | 99.9 | 99.9 |

Example 3

A solution of myosmine (20 mmol, 2.924 g), D-Glucose (30 mmol, 5.405 g) nicotinamide adenine dinucleotide phosphate sodium salt (0.2 mmol, 157 mg), enzyme IRED_A (available from Enzymicals) cell free extract lyophilizate (1.0 g), glucose dehydrogenase (2000 U, 40 mg) in pH7.5 100 mM sodium phosphate buffer (200 mL) was mixed by an overhead stirrer at 200 rpm at 30° C. for 24 hours. The solution was analysed for nornicotine during the course of the reaction with HPLC showing 77% conversion after 8 hours, and over 99% conversion after 24 h with 98.7% e.e. (S)-Nornicotine. This solution was then treated with 37% formaldehyde solution (8.1 g) and formic acid (2.8 g) at 80° C. for 4 h, with the reaction being complete after 2 h. After cooling, 6 g solid sodium hydroxide was added (pH 12.7) and the mixture extracted with 2×75 ml MTBE. After drying over sodium sulphate, the solvent was removed to afford 2.25 g crude (S)-nicotine which was >99% pure by HPLC (area % at 260 nm) and had 98.7% enantiomeric excess.

Example 4

A solution of myosmine (20 mmol, 2.924 g), D-Glucose (30 mmol, 5.405 g) nicotinamide adenine dinucleotide phosphate sodium salt (0.2 mmol, 157 mg), enzyme IRED_B (available from Enzymicals) cell free extract lyophilizate (0.5 g), glucose dehydrogenase (2000 U, 40 mg) in pH7.5 100 mM sodium phosphate buffer (200 mL) was mixed by overhead stirrer at 200 rpm at 30° C. for 24 hours. The solution was analysed for nornicotine during the course of the reaction with HPLC showing 91% conversion after 4 hours, and over 99% conversion after 6 hours. After 24 hours the (S)-Nornicotine was 98.2% e.e. This solution was then treated with paraformaldehyde (3 g) and formic acid (2.8 g) at 80° C. for 6 h, with the reaction being complete after 4 h. After cooling, 6 g solid sodium hydroxide was added (pH 12.7) and the mixture extracted with 2×75 ml MTBE. After drying over sodium sulphate, the solvent was removed to afford 2.31 g crude (S)-nicotine which was >99% pure by HPLC (area % at 260 nm) and had 98.3% enantiomeric excess.

Example 5

This example demonstrates the enantioselectivity and conversion rate at high substrate concentrations. This example was carried out in a similar manner to example 1 except that all reactions used glucose 1.5 equivs, NADP (1% relative to the myosmine), imine reductase, specifically IRED_C available from Enzymicals (4.5 mg/ml cell free extract, GDH (10 U/ml per 250 mM of myosmine concentration), sodium phosphate buffer pH7.5 100 mM over a 24 hour time period. The results are shown below.

TABLE 5

| | Concentration of myosmine starting material | Conversion [%] | Enantiomeric Excess [% S] |
|---|---|---|---|
| i | 250 mM | 99.9 | 99.7 |
| ii | 400 mM | 99.6 | 99.8 |
| iii | 600 mM | 68.8 | 99.8 |
| iv | 800 mM | 56.5 | 99.7 |
| v | 1000 mM | 52.4 | 99.6 |

Example 6

This example demonstrates the enantioselectivity and conversion rate on a larger scale.

A solution of myosmine (400 mmol, 58.5 g), D-Glucose (600 mmol, 118.9 g) nicotinamide adenine dinucleotide phosphate sodium salt (4 mmol, 3.15 g), enzyme IRED_C (available from enzymicals) cell free extract lyophilisate (10.0 g), glucose dehydrogenase CFE (0.32 g) in pH7.5 100 mM sodium phosphate buffer (1000 mL) was mixed with an overhead stirrer at 200 rpm at 30° C. for 24 hours. The solution was analysed for nornicotine after 24 hours with HPLC and showed over 98% conversion.

Details of the workup are as follows: the biocatalytic reaction mixture was acidified with concentrated sulphuric acid to pH 1-2, then heated to 90° C. for 20 minutes to precipitate all the proteins. Proteins were filtered out of the mixture over Celite. The resulting clear solution was basified with 40% NaOH solution to pH>11 and extracted four times with 500 mL methyl tert-butyl ether (MTBE). The combined MTBE phases were dried over anhydrous magnesium sulfate and the solvent evaporated. The isolated yield of nornicotine was 41.1 g (70%) as a brown-yellow liquid.

A separate sample of the nornicotine reaction mixture prior to work up and isolation was taken through to the methylation step. Specifically, without isolation of the nornicotine, to the biocatalytic reaction mixture, paraformaldehyde (60 g) and formic acid (49.2 g) were added. The reaction was heated to 85° C. and stirred vigorously to form (S)-nicotine.

Example 7

The general experimental method to form (S)-nicotine was as follows. Biocatalysis of myosmine into (S)-nornicotine using IRED_C (available from Enzymicals) was conducted at a concentration of 400 mM myosmine. Either the (S)-nornicotine was isolated by way of extraction with methyl-tert butyl ether and removal of the solvent, or the aqueous solution from the biocatalysis was heated at 90° C. for 15 min to precipitate proteins, then after cooling the mixture was acidified to pH 1-2 with sulfuric acid, the precipitated protein removed by filtration through Celite, and the solution then neutralised with aqueous sodium hydroxide to about pH7.

Example 7a

Crude isolated nornicotine from the enzyme reduction of myosmine (92 g) was added to 800 ml water. Paraformaldehyde (74 g, 4 eq) and formic acid (58 g, 2 eq) were added. The mixture was gradually warmed to 80-85 degrees C. HPLC analysis after 2 h indicated completion of the reaction. The mixture was kept at the same temperature for a further 2 h and then cooled to room temperature. 50% Sodium hydroxide solution was added to obtain a pH of approximately 13. The mixture was extracted with 2×500 ml MTBE and dried over sodium sulphate. The solvent was removed and the crude (S)-nicotine distilled under vacuum. After a forerun of about 4 g, 87 g of purified nicotine was obtained (>99% by HPLC and 99.6% ee by chiral HPLC).

Example 7b

To 2.5 litres of aqueous nor-nicotine solution from the same biocatalysis as used in Example 1 (5.63 g/100 ml) was added paraformaldehyde (112.5 g, 4 eq) and formic acid (88 g, 2 eq). The mixture was gradually heated to 80-85 degrees C., with reaction beginning at about 70 degrees C. with some foaming due to gas evolution. After 1 h at 80-85 degrees C., HPLC indicated the reaction to be complete. The reaction was heated for 4 h in total and then cooled. The mixture was basified with 50% sodium hydroxide solution and extracted with MTBE (800 ml then 500 ml). After drying, the crude mixture was distilled to give 118.7 g (S)-nicotine (>99% by HPLC and 99.5% ee by HPLC).

Example 7c

To 2.5 litres of aqueous nor-nicotine solution from the same biocatalysis as used in Example 1 (5.63 g/100 ml) was added 37% formaldehyde solution (290 ml, ~4 eq) and formic acid (88 g, 2 eq). The mixture was gradually heated to 80-85 degrees C., with reaction beginning at about 60 degrees C. with some foaming due to gas evolution. After 1 h at 80-85 degrees C., HPLC indicated the reaction to be complete. The reaction was heated for 4 h in total and then cooled. The mixture was basified with 50% sodium hydroxide solution and extracted with MTBE (800 ml then 500 ml). After drying, the crude mixture was distilled to give 119.1 g (S)-nicotine (>99% by HPLC and 99.5% ee by HPLC).

Example 8

A solution of myosmine (298 g) and glucose monohydrate (505 g) was made in 0.1M dipotassium hydrogen phosphate buffer (6 L). Amberlite IR-120 resin (2 kg, wet) was added as the ion exchange resin and the solution adjusted to pH7 with 12M sodium hydroxide (about 0.3 L), then stirred overnight at 25° C. to ensure a stable pH. Glucose dehydrogenase GDH-102 (6 g), beta-NADP+(6 g), and enzyme IRED-20 available from the Almac Group (30 g) were added, then the mixture stirred at 150 rpm while held at 25° C. with the pH maintained in the range 6.8-7.0 through additions of 4M postassium hydroxide. After 72 h the solution was decanted and the Amberlite resin was washed with deionized water (3×3 L). Then Amberlite resin was transferred to a column and further washed with deionized water (4 L), then shaken for 3 hours with 2M ammonia solution (4 L) and further washed with 2M ammonia (10 L). The combined solutions were concentrated under reduced pressure to dryness to give (S)-Nornicotine (131.2 g) as a yellow liquid. In order to recover further nornicotine out of the reaction mixture, reactivated Amberlite resin (2 kg) was added to it and the mixture stirred overnight at room temperature. The same treatment was repeated as above to recover further (S)-Nornicotine (59.8 g) bringing the total yield to 191.0 g. The above two batches were converted into (S)-nicotine separately. For the larger batch the (S)-nornicotine (126.2 g of) was combined with paraformaldehyde (154.5 g) and formic acid (118 g) in water (1 L) and the resulting stirred mixture heated to 85° C. overnight. The mixture was then cooled to 0° C., and adjusted to pH 14 with 12M sodium hydroxide. The mixture was extracted with methyl tert-butyl ether (3×8 vols). The organic phase was dried with anhydrous magnesium sulfate and concentrated to dryness to give crude (S)-nicotine as a yellow liquid (131.2 g). The second batch of (S)-nornicotine (59.8 g) had likewise been transformed into crude (S)-nicotine (60.7 g) in the same manner making a total yield of crude nicotine of 191.9 g. These were combined and distilled under reduced pressure (b.p. 70-77° C. at 0.53-0.67 mbar) to provide (S)-nicotine (174.5 g) as a colourless liquid with an enantiomeric excess of 99.38% as determined by HPLC, and a chemical purity of 99.96%, as determined by HPLC. Further of the process used to measure enantiomeric excess and chemical purity are given below.

Enantiomeric purity by HPLC: using a Chiracel OD-H column eluting with n-hexane and 1-butanol in a ratio of 95:5 and containing 0.1% diethylamine. The (R)-enantiomer eluted at 6.1 min and the (S)-enantiomer at 5.6 min. The enantiomeric excess is determined from the area of the peaks identified according to the equation [(S)−(R)]/((S)+(R)]. The enantiomeric excess was thus determined as 99.38%.

Chemical purity by HPLC: Using an X-Bridge C18 column with an eluant comprising a mixture of (i) 20 mM ammonium bicarbonate in water (pH=8.7) and (ii) acetonitrile in a gradient programme of 0-10 mins at 95:5, 10-13 mins at 70:30; 13-16 mins at 10:90; and subsequently 95:5. Temperature was 35 degrees C. The conditions of the detector were of UV absorption at a wavelength of 260 nm. A single impurity at 12.132 minutes at 0.04% area was found versus nicotine at 9.925 mins. With a single impurity at 0.04% area the purity was deemed as 99.96%. In comparison, prior to distillation the weighted average of the two batches used was 99.70%.

The invention claimed is:

1. A process of making (S)-nicotine comprising the steps of:
   (i) reducing myosmine with an enzyme with imine reductase activity to form (S)-nornicotine; and
   (ii) methylating the (S)-nornicotine formed from step (i) to form (S)-nicotine;
   wherein step (ii) is carried out by way of reductive methylation; and
   wherein in step (ii) the (S)-nornicotine is reductively methylated, using formaldehyde or a formaldehyde-based compound in the presence of a reductant.

2. The process of claim 1 wherein the formaldehyde is introduced as part of an aqueous solution.

3. The process of claim 1 wherein the formaldehyde-based compound is a dimer of formaldehyde, a polymer of formaldehyde, or an acetal of formaldehyde.

4. The process of claim 1, wherein the reductant is formic acid, sodium cyanoborohydride, or palladium/hydrogen.

5. The process of claim 1, wherein the reductant is formic acid.

6. The process of claim 1, wherein the process is carried out without isolation of the (S)-nornicotine formed from step (i).

7. The process of claim 1, wherein in step (i) the (S)-nornicotine is formed as part of an aqueous solution, and wherein step (ii) comprises methylating the (S)-nornicotine contained within the aqueous solution.

8. The process according to claim 7, wherein in step (ii) the (S)-nornicotine is reductively methylated using formaldehyde introduced as part of an aqueous solution.

9. The process of claim 1, wherein the (S)-nicotine is obtained with an enantiomeric excess of at least 90%, preferably at least 95%, more preferably at least 98%, most preferably at least 99%.

10. A process for producing a pharmaceutical composition, comprising forming (S)-nicotine according to the process of claim 1, and including the (S)-nicotine in the pharmaceutical composition together with one or more pharmaceutical excipients.

11. The process of claim 10, wherein the pharmaceutical composition is a transdermal patch, a lozenge, or an inhalation formulation.

12. A process for producing a formulation for an electronic cigarette device, comprising forming (S)-nicotine according to the process of claim 1, and including the (S)-nicotine in a solvent with one or more additives.

13. The process of claim 2, wherein the reductant is formic acid, sodium cyanoborohydride, or palladium/hydrogen.

14. The process of claim 2, wherein the reductant is formic acid.

* * * * *

SEQUENCE LISTING

```
<160> NUMBER OF SEQ ID NOS: 4

<210> SEQ ID NO 1
<211> LENGTH: 302
<212> TYPE: PRT
<213> ORGANISM: Verrucosispora maris

<400> SEQUENCE: 1

Met His His His His His His Ala Ala Asp Ser Arg Ala Pro Val Thr
1               5                   10                  15

Val Ile Gly Leu Gly Ala Met Gly Ser Ala Leu Ala Arg Ala Phe Leu
            20                  25                  30

Ala Ala Gly His Pro Thr Thr Val Trp Asn Arg Ser Pro Asp Lys Ala
        35                  40                  45

Asp Asp Leu Val Gly Gln Gly Ala Val Arg Ala Ala Thr Val Ala Asp
    50                  55                  60

Ala Met Ser Ala Gly Asn Leu Ile Val Ile Cys Val Leu Asp Tyr Arg
65                  70                  75                  80

Ala Met Arg Glu Ile Ile Asp Ser Thr Gly His Ser Pro Ala Asp Arg
                85                  90                  95

Val Ile Val Asn Leu Thr Ser Gly Thr Pro Gly Asp Ala Arg Ala Thr
            100                 105                 110

Ala Ala Trp Ala Gln Glu Gln Gly Met Glu Tyr Ile Asp Gly Ala Ile
        115                 120                 125

Met Ala Thr Pro Ser Met Ile Gly Ser Glu Glu Thr Leu Ile Phe Tyr
    130                 135                 140

Gly Gly Pro Gln Glu Val Tyr Asp Ala His Ala Asp Thr Leu Arg Ser
145                 150                 155                 160

Ile Ala Gly Ala Gly Thr Tyr Leu Gly Glu Glu Pro Gly Leu Pro Ser
                165                 170                 175
```

Leu Tyr Asp Val Ala Leu Leu Gly Leu Met Trp Thr Thr Trp Ala Gly
                180                 185                 190

Phe Met His Ser Ala Ala Leu Leu Ala Ser Glu Lys Val Pro Ala Ala
                195                 200                 205

Ala Phe Leu Pro Tyr Ala Gln Ala Trp Phe Glu Tyr Val Ile Ser Pro
    210                 215                 220

Glu Val Pro Asn Leu Ala Thr Gln Val Asp Thr Gly Ala Tyr Pro Asp
225                 230                 235                 240

Asn Asp Ser Thr Leu Gly Met Gln Thr Val Ala Ile Glu His Leu Val
                245                 250                 255

Glu Ala Ser Arg Thr Gln Gly Val Asp Pro Thr Leu Pro Glu Phe Leu
                260                 265                 270

His Ala Arg Ala Glu Gln Ala Ile Arg Arg Gly His Ala Gly Asp Gly
                275                 280                 285

Phe Gly Ala Val Phe Glu Val Leu Arg Ala Pro Ala Ala Gln
    290                 295                 300

<210> SEQ ID NO 2
<211> LENGTH: 296
<212> TYPE: PRT
<213> ORGANISM: Verrucosispora maris

<400> SEQUENCE: 2

Met Ala Ala Asp Ser Arg Ala Pro Val Thr Val Ile Gly Leu Gly Ala
1               5                   10                  15

Met Gly Ser Ala Leu Ala Arg Ala Phe Leu Ala Ala Gly His Pro Thr
                20                  25                  30

Thr Val Trp Asn Arg Ser Pro Asp Lys Ala Asp Asp Leu Val Gly Gln
            35                  40                  45

Gly Ala Val Arg Ala Ala Thr Val Ala Asp Ala Met Ser Ala Gly Asn
        50                  55                  60

Leu Ile Val Ile Cys Val Leu Asp Tyr Arg Ala Met Arg Glu Ile Ile
65                  70                  75                  80

Asp Ser Thr Gly His Ser Pro Ala Asp Arg Val Ile Val Asn Leu Thr
                85                  90                  95

Ser Gly Thr Pro Gly Asp Ala Arg Ala Thr Ala Ala Trp Ala Gln Glu
                100                 105                 110

Gln Gly Met Glu Tyr Ile Asp Gly Ala Ile Met Ala Thr Pro Ser Met
            115                 120                 125

Ile Gly Ser Glu Glu Thr Leu Ile Phe Tyr Gly Gly Pro Gln Glu Val
        130                 135                 140

Tyr Asp Ala His Ala Asp Thr Leu Arg Ser Ile Ala Gly Ala Gly Thr
145                 150                 155                 160

Tyr Leu Gly Glu Glu Pro Gly Leu Pro Ser Leu Tyr Asp Val Ala Leu
                165                 170                 175

Leu Gly Leu Met Trp Thr Thr Trp Ala Gly Phe Met His Ser Ala Ala
                180                 185                 190

Leu Leu Ala Ser Glu Lys Val Pro Ala Ala Phe Leu Pro Tyr Ala
            195                 200                 205

Gln Ala Trp Phe Glu Tyr Val Ile Ser Pro Glu Val Pro Asn Leu Ala
    210                 215                 220

Thr Gln Val Asp Thr Gly Ala Tyr Pro Asp Asn Asp Ser Thr Leu Gly
225                 230                 235                 240

Met Gln Thr Val Ala Ile Glu His Leu Val Glu Ala Ser Arg Thr Gln

-continued

```
                    245                 250                 255
Gly Val Asp Pro Thr Leu Pro Glu Phe Leu His Ala Arg Ala Glu Gln
            260                 265                 270

Ala Ile Arg Arg Gly His Ala Gly Asp Gly Phe Gly Ala Val Phe Glu
            275                 280                 285

Val Leu Arg Ala Pro Ala Ala Gln
            290                 295

<210> SEQ ID NO 3
<211> LENGTH: 310
<212> TYPE: PRT
<213> ORGANISM: Mesorhizobium sp. L48C026A00

<400> SEQUENCE: 3

Met His His His His His Ala Ser Asn Val Cys Val Leu Gly Ala
 1               5                  10                  15

Gly Arg Met Gly Ser Ser Ile Ala Arg Thr Leu Leu Asp Arg Gly Tyr
            20                  25                  30

Pro Thr Trp Val Trp Asn Arg Thr Ala Ala Lys Cys Glu Pro Leu Ala
            35                  40                  45

Ala Leu Gly Ala Lys Val Ala Ser Ser Val Gln Glu Gly Ile Gln Ala
        50                  55                  60

Ala Glu Val Val Ile Ile Asn Val Leu Asp Tyr Ala Ala Ser Asp Ala
65                  70                  75                  80

Leu Leu Lys Arg Asp Gly Ile Ala Ser Leu Ala Gly Lys Ala Val
                85                  90                  95

Val Gln Leu Thr Ser Gly Ser Pro Arg Leu Ala Arg Glu Glu Ala Arg
            100                 105                 110

Trp Val Glu Ala His Gly Ala Gly Tyr Leu Asp Gly Ala Ile Met Ala
            115                 120                 125

Thr Pro Asp Phe Ile Gly Lys Pro Glu Thr Ala Met Leu Tyr Ser Gly
        130                 135                 140

Ser Arg Asp Val Tyr Glu Lys His Lys Pro Leu Leu Phe Ala Leu Gly
145                 150                 155                 160

Gly Gly Thr Asn Tyr Val Gly Glu Leu Pro Gly Gln Ala Ser Ala Leu
                165                 170                 175

Asp Thr Ala Leu Leu Thr Gln Met Trp Gly Gly Leu Phe Gly Ala Leu
            180                 185                 190

Gln Gly Met Ala Val Ala Glu Ala Glu Gly Leu Asp Leu Glu Thr Phe
        195                 200                 205

Arg Asn His Leu Ser Ala Phe Lys Pro Val Val Asp Ala Ser Leu Phe
210                 215                 220

Asp Leu Val Asp Arg Thr Asn Ala Arg Arg Phe Ala Gly Asp Ala
225                 230                 235                 240

Thr Leu Ala Ser Leu Gly Ala His Tyr Ser Ala Phe Gln His Leu Leu
                245                 250                 255

Glu Ala Cys Glu Glu Arg Gly Leu Asp Ala Ala Met Pro Arg Ala Met
            260                 265                 270

Asp Met Ile Phe Arg Gln Ala Leu Ser Leu Gly Ser Met Glu Asp Asp
            275                 280                 285

Leu Ala Ser Leu Ala Leu Leu Phe Arg Asn Gly Ser Pro Arg Gln Ser
        290                 295                 300

Arg Glu Pro Ala Asn Ala
305                 310
```

```
<210> SEQ ID NO 4
<211> LENGTH: 304
<212> TYPE: PRT
<213> ORGANISM: Mesorhizobium sp. L48C026A00

<400> SEQUENCE: 4

Met Ala Ser Asn Val Cys Val Leu Gly Ala Gly Arg Met Gly Ser Ser
1               5                   10                  15

Ile Ala Arg Thr Leu Leu Asp Arg Gly Tyr Pro Thr Trp Val Trp Asn
            20                  25                  30

Arg Thr Ala Ala Lys Cys Glu Pro Leu Ala Ala Leu Gly Ala Lys Val
        35                  40                  45

Ala Ser Ser Val Gln Glu Gly Ile Gln Ala Ala Glu Val Val Ile Ile
    50                  55                  60

Asn Val Leu Asp Tyr Ala Ala Ser Asp Ala Leu Leu Lys Arg Asp Gly
65                  70                  75                  80

Ile Ala Ser Ala Leu Ala Gly Lys Ala Val Val Gln Leu Thr Ser Gly
            85                  90                  95

Ser Pro Arg Leu Ala Arg Glu Glu Ala Arg Trp Val Glu Ala His Gly
            100                 105                 110

Ala Gly Tyr Leu Asp Gly Ala Ile Met Ala Thr Pro Asp Phe Ile Gly
            115                 120                 125

Lys Pro Glu Thr Ala Met Leu Tyr Ser Gly Ser Arg Asp Val Tyr Glu
130                 135                 140

Lys His Lys Pro Leu Leu Phe Ala Leu Gly Gly Thr Asn Tyr Val
145                 150                 155                 160

Gly Glu Leu Pro Gly Gln Ala Ser Ala Leu Asp Thr Ala Leu Leu Thr
            165                 170                 175

Gln Met Trp Gly Gly Leu Phe Gly Ala Leu Gln Gly Met Ala Val Ala
            180                 185                 190

Glu Ala Glu Gly Leu Asp Leu Glu Thr Phe Arg Asn His Leu Ser Ala
            195                 200                 205

Phe Lys Pro Val Val Asp Ala Ser Leu Phe Asp Leu Val Asp Arg Thr
210                 215                 220

Asn Ala Arg Arg Phe Ala Gly Asp Asp Ala Thr Leu Ala Ser Leu Gly
225                 230                 235                 240

Ala His Tyr Ser Ala Phe Gln His Leu Leu Glu Ala Cys Glu Glu Arg
            245                 250                 255

Gly Leu Asp Ala Ala Met Pro Arg Ala Met Asp Met Ile Phe Arg Gln
            260                 265                 270

Ala Leu Ser Leu Gly Ser Met Glu Asp Asp Leu Ala Ser Leu Ala Leu
            275                 280                 285

Leu Phe Arg Asn Gly Ser Pro Arg Gln Ser Arg Glu Pro Ala Asn Ala
            290                 295                 300
```